(12) United States Patent
Lewin et al.

(10) Patent No.: US 7,335,763 B2
(45) Date of Patent: Feb. 26, 2008

(54) HERPESVIRUS RIBOZYMES AND VECTORS

(75) Inventors: Alfred Samuel Lewin, Gainesville, FL (US); David Clair Bloom, Gainesville, FL (US); Gregory Scott Schultz, Gainesville, FL (US); Sonal Sanjeen Tuli, Gainesville, FL (US); Jia Liu, Gainesville, FL (US)

(73) Assignee: University of Florida Research Foundation, Inc., Gainsville, FL (US)

( * ) Notice: Subject to any disclaimer, the term of this patent is extended or adjusted under 35 U.S.C. 154(b) by 484 days.

(21) Appl. No.: 10/808,042

(22) Filed: Mar. 24, 2004

(65) Prior Publication Data

US 2006/0116340 A1 Jun. 1, 2006

Related U.S. Application Data

(60) Provisional application No. 60/457,279, filed on Mar. 25, 2003.

(51) Int. Cl.
*C07H 21/04* (2006.01)

(52) U.S. Cl. .................................................. 536/24.5

(58) Field of Classification Search ................ 536/24.5
See application file for complete search history.

(56) References Cited

U.S. PATENT DOCUMENTS

| 6,277,621 B1 * | 8/2001 | Horsburgh et al. ...... 435/235.1 |
| 2005/0096282 A1 * | 5/2005 | Lewin et al. .................. 514/44 |

FOREIGN PATENT DOCUMENTS

WO    WO 00/66780    * 11/2000

* cited by examiner

*Primary Examiner*—Brian Whiteman
(74) *Attorney, Agent, or Firm*—Timothy H. Van Dyke; Beusse Wolter Sanks Mora & Maire

(57) ABSTRACT

Hammerhead ribozymes that target components critical to HSV replication (ICP4, UL20, UL30, and UL54) were synthesized and shown to efficiently cleave target RNA encoding a portion of these components in in vitro assays. Several cloned cell lines stably expressing these ribozymes were established. HSV-mediated plaque formation was dramatically reduced in cells stably transfected with an anti-HSV ribozyme compared to non-transfected cells.

8 Claims, 4 Drawing Sheets

SEQUENCE LISTING

```
<160> NUMBER OF SEQ ID NOS: 18

<210> SEQ ID NO 1
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 1
aaggucugau gagcgcuucg gcgcgaaacg aac                           33

<210> SEQ ID NO 2
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 2
```
gaacucugau gagcgcuucg gcgcgaaaca aaa                          33

<210> SEQ ID NO 3
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 3
cggaacugau gagcgcuucg gcgcgaaacg cga                          33

<210> SEQ ID NO 4
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 4
uucugcugau gagcgcuucg gcgcgaaacg aga                          33

<210> SEQ ID NO 5
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 5
ugcaucugau gagcgcuucg gcgcgaaacc ugu                          33

<210> SEQ ID NO 6
<211> LENGTH: 33
<212> TYPE: RNA
<213> ORGANISM: ARTIFICIAL
<220> FEATURE:
<223> OTHER INFORMATION: synthetic ribozyme

<400> SEQUENCE: 6
acgaacugau gagcgcuucg gcgcgaaagg aug                          33

<210> SEQ ID NO 7
<211> LENGTH: 12
<212> TYPE: RNA
<213> ORGANISM: HERPES SIMPLEX VIRUS

<400> SEQUENCE: 7
cauccucuuc gu                                                 12

<210> SEQ ID NO 8
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 8
cuucauccuc gu                                                 12

<210> SEQ ID NO 9
<211> LENGTH: 12
<212> TYPE: RNA
<213> ORGANISM: HERPES SIMPLEX VIRUS

```
<400> SEQUENCE: 9
uuuugucagu uc                                                    12

<210> SEQ ID NO 10
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 10
uuucgugagc uc                                                    12

<210> SEQ ID NO 11
<211> LENGTH: 12
<212> TYPE: RNA
<213> ORGANISM: HERPES SIMPLEX VIRUS

<400> SEQUENCE: 11
ucgcgucuuc cg                                                    12

<210> SEQ ID NO 12
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 12
ucacgccucc cg                                                    12

<210> SEQ ID NO 13
<211> LENGTH: 12
<212> TYPE: RNA
<213> ORGANISM: HERPES SIMPLEX VIRUS

<400> SEQUENCE: 13
guucgucacc uu                                                    12

<210> SEQ ID NO 14
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 14
auucgugaca uu                                                    12

<210> SEQ ID NO 15
<211> LENGTH: 12
<212> TYPE: RNA
<213> ORGANISM: HERPES SIMPLEX VIRUS

<400> SEQUENCE: 15
ucucguccag aa                                                    12

<210> SEQ ID NO 16
<211> LENGTH: 12
<212> TYPE: RNA
<213> ORGANISM: ARTIFICIAL
<220> FEATURE:
```

-continued

```
<223> OTHER INFORMATION: synthetic sequence containing site-directed
      mutations

<400> SEQUENCE: 16
ucccgccccg aa                                                           12

<210> SEQ ID NO 17
<211> LENGTH: 12
<212> TYPE: RNA
<213> ORGANISM: HERPES SIMPLEX VIRUS

<400> SEQUENCE: 17
acaggucaug ca                                                           12

<210> SEQ ID NO 18
<211> LENGTH: 12
<212> TYPE: RNA
<213> ORGANISM: ARTIFICIAL
<220> FEATURE:
<223> OTHER INFORMATION: synthetic sequence containing site-directed
      mutations

<400> SEQUENCE: 18
acaagugaug ca                                                           12
```

HERPESVIRUS RIBOZYMES AND VECTORS

CROSS-REFERENCE TO RELATED APPLICATIONS

The present application claims the priority of U.S. provisional patent application Ser. No. 60/457,279 filed Mar. 25, 2003.

FIELD OF THE INVENTION

This invention relates generally to the fields of molecular biology and medicine. More particularly, the invention relates to compositions and methods of controlling acute and recurrent viral infections using ribozymes that prevent viral replication by cleaving mRNAs encoding viral proteins.

BACKGROUND

Herpes simplex virus (HSV) is a nuclear replicating, icosahedral, enveloped DNA virus that can cause blisters and sores almost anywhere on the skin, usually around the mouth and nose, or on the genitals and buttocks. The sores associated with HSV infections may be painful and unsightly. For immunosupressed patient and neonates, HSV infection can be serious and sometimes fatal.

HSV exists in two forms, HSV-1, which is usually associated with infections of the lips, mouth, and face, and, HSV-2, which is commonly associated with infections of the genitalia. Occasionally HSV can infect the eye, causing blindness in some cases. Although active HSV infections typically resolve without treatment, because HSV latently infects nerve cells, active infections tend to recur.

There is no known cure for HSV infection. Vaccines for preventing HSV infection in humans are not currently available. Coventional treatment of HSV infection is oral administration of anti-viral medications such as acyclovir, famciclovir, or valacyclovir. These are used to treat active outbreaks and to suppress recurrences. Although generally safe and effective, these drugs cannot eliminate a latent HSV infection.

Accordingly, what is needed is a new treatment modality that continuously produces antiviral agents that block replication of herpes viruses in sensory neurons where they remain latent, diminishing the likelihood of viral reactivation. Such a new treatment modality could also protect against viral replication in the cornea, where recurrent infections lead to scarring and blindness.

SUMMARY

The invention relates to the development of ribozymes that can be used to treat HSV infections, as well as methods for producing and delivering such ribozymes. Hammerhead ribozymes that target components critical to HSV replication (ICP4, UL20, UL30, and UL54) were synthesized and shown to efficiently cleave target RNA encoding a portion of these components in in vitro assays. Several cloned cell lines stably expressing these ribozymes were established. HSV-mediated plaque formation was dramatically reduced in cells stably transfected with an anti-HSV ribozyme compared to non-transfected cells. The number of plaque forming units (pfu) was also significantly reduced in cultures transfected with an anti-HSV ribozyme compared to non-transfected cells. In cells transiently transfected with an anti-HSV ribozyme, target viral mRNA levels were much lower than in control cells. Thus, the ribozymes of the invention are also able to cleave target HSV mRNA and reduce virion production in living cells.

Accordingly, the invention features a ribozyme that specifically cleaves a target RNA sequence encoded by a HSV gene essential or important for efficient HSV replication or packaging. The gene can be, e.g., UL20, UL30, UL54, or ICP4. The ribozyme can be in a hammerhead configuration, within a vector, and/or within a cell. Examples of such riboymes include those including SEQ ID NOs: 1, 3, 5, and/or 6.

In another aspect, the invention features a method for impairing HSV replication in a cell. This method includes the step of expressing in the cell, in an amount effective to reduce HSV replication in the cell, a ribozyme that specifically cleaves a target RNA sequence encoded by a HSV gene such as UL20, UL30, UL54, or ICP4.

The invention further includes a ribozyme-resistant cell for producing a HSV expression vector encoding an anti-HSV ribozyme. The cell includes at least one nucleotide sequence encoding a portion of an HSV gene, the nucleotide sequence having been modified to not be cleavable by the ribozyme.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

DETAILED DESCRIPTION

Figure 1:
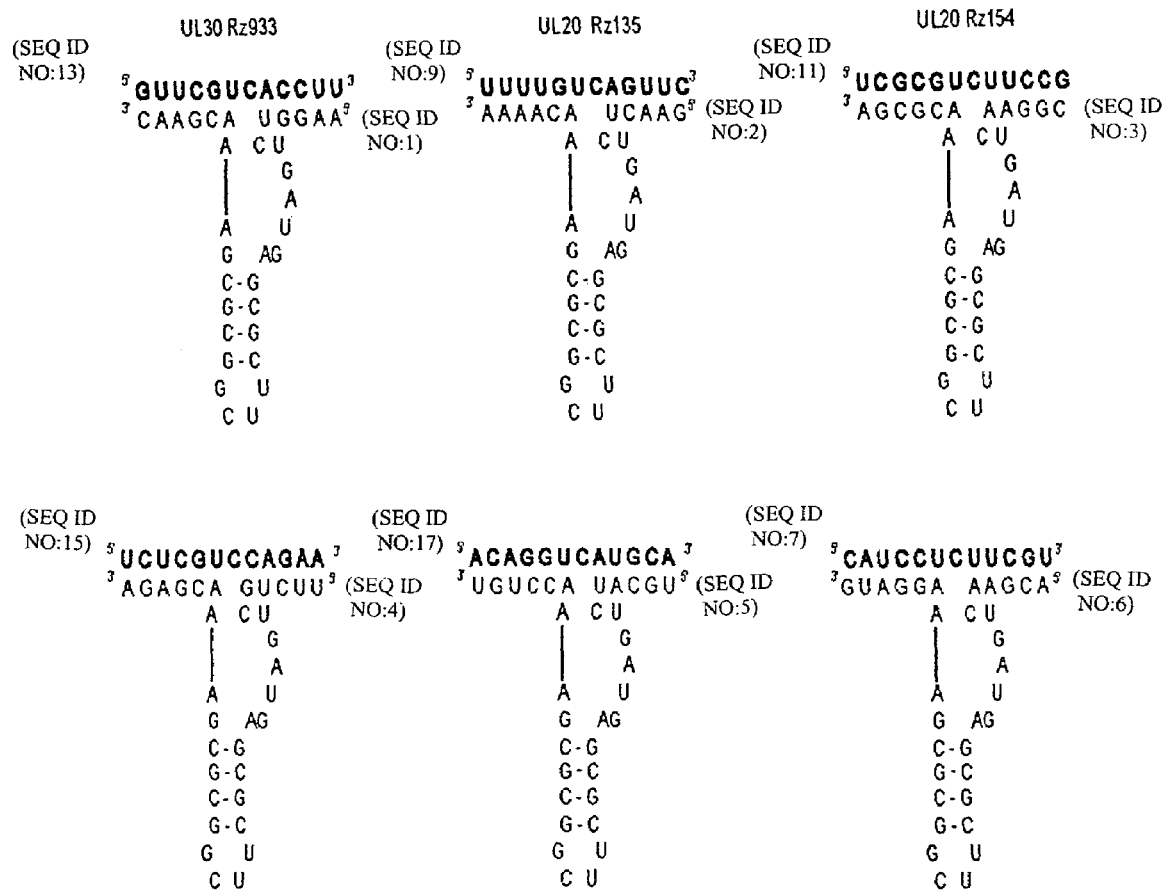
FIG. 1 is a diagram showing the RNA nucleotide sequences of ribozymes directed against HSV genes UL20, UL30, UL54 and ICP4. The corresponding nucleotide sequences of the HSV target RNAs are indicated in boldface.

The invention provides compositions and methods for inhibiting replication of HSV-1 and HSV-2 using ribozymes that cleave RNA targets encoded by the HSV genes UL20, UL30, UL54 and ICP4. Also provided are HSV expression vectors including nucleic acid sequences encoding ribozymes directed against RNA targets in these HSV genes, ribozyme-resistant cells useful for production and packaging of HSV viral vectors expressing HSV-targeting ribozymes, and methods for using such vectors to reduce HSV replication, e.g., in cells susceptible to recurrent HSV infection.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

HSV-Targeting Ribozymes

The invention provides ribozymes that specifically cleave a target RNA sequence encoded by an HSV gene essential for replication. The RNA targeted can be any that is essential or important for HSV replication, e.g., one that encodes a protein necessary for efficent genome replication or viral assembly. Exemplary targets include RNAs encoding UL20, UL30, UL54 and ICP4. To inhibit replication of HSV in a cell, ribozymes against 1, 2, 3, 4 or more such targets can be used. It is preferred that at least 2 or 3 different ribozymes be used simultaneously to prevent mutation rendering ribozyme resistance.

Several forms of naturally-occurring and synthetic ribozymes are known, including Group I and Group II introns, RNaseP, hairpin ribozymes and hammerhead ribozymes (Lewin A S and Hauswirth W W, Trends in Molecular Medicine 7: 221-228, 2001). Any form suitable for use in the invention might be used. For example, ribozymes of the invention can be in a hammerhead configuration.

Hammerhead ribozymes are advantageous because they can be engineered to selectively bind and cleave a complementary mRNA molecule, then release the fragments, repeating the process with the efficiency of a protein enzyme. As shown in examples below, they have proven to be highly effective at cleaving target RNA sequences selective for HSV-1 genes, including UL20, UL30, UL54 and ICP4. Because hammerhead ribozymes cleave after UX dinucleotides, where X can be any ribonucleotide except guanosine, specific target sequences should have this sequence. A large number are present in HSV RNA. In practice, NUX triplets (typically GUC, CUC or UUC) are required in the target mRNA. Such targets are used to design an antisense RNA of 12 or 13 nucleotides surrounding that site, but skipping the C, which does not form a conventional base pair with the ribozyme.

Preferred targets of the ribozymes of the invention are those RNA encoding HSV genes that include AUC, GUC, CUC or UUC triplets as these have proven to been the best substrates for cleavage by hammerhead ribozymes. The most preferred target RNAs include GUCUU or GUCUA as experiments performed using these as target have all proven successful except when the ribozyme folded incorrectly due to the remainder of the target sequence (i.e. base pairing between one of the "arms" of the ribozyme and the catalytic core of the ribozyme).

Figure 4:
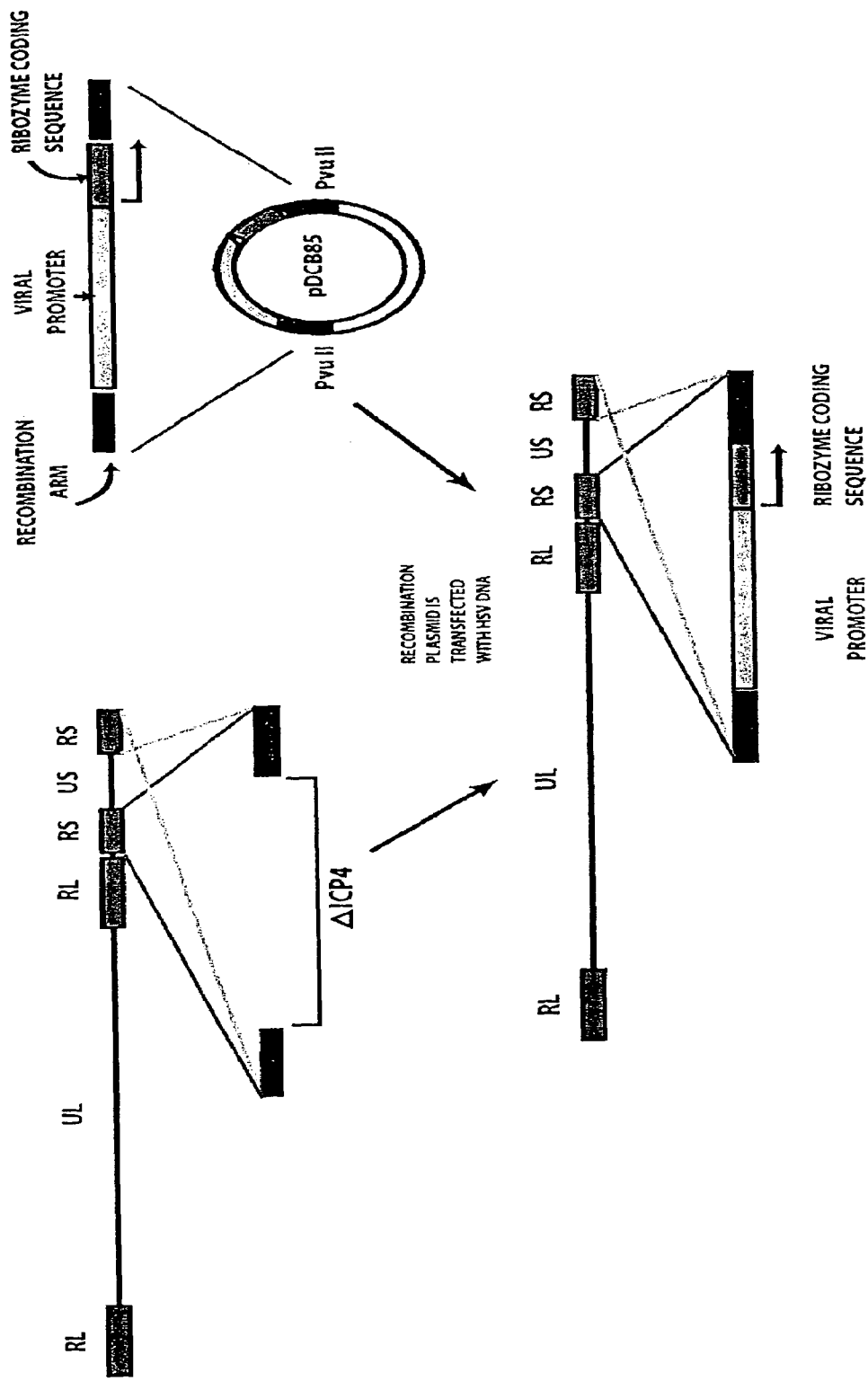
FIG. 4 is a highly schematic illustration of the construction of HSV-vectored ribozymes.

FIG. 4 shows examples of the design of several hammerhead ribozymes of the invention, aligned with the hammerhead portions of the molecules facing their respective RNA targets. Although each of these ribozymes is designed in a 6-4-5 stem-loop-stem configuration, any other configuration suitable for the purpose might be used. In general, because the chemical cleavage step is rapid and the release step is rate-limiting, speed and specificity are enhanced if the hybridizing "arms" of the ribozyme (helices I and III) are relatively short, e.g., about 5 or 6 nucleotides. Suitability of the design of a particular configuration can be determined empirically, using various assays as described below.

Secondary structure in RNA can interfere with the ability of a ribozyme to bind to the target site. For this reason, some synthetic ribozymes are more efficient than others at cleaving their targets. Structure-predicting algorithms such as MFOLD can be used to rule out certain target sites, but ultimately accessibility must be determined experimentally. To determine the cutting efficiency of a particular ribozyme, a series of in vitro tests can be performed as described in Shaw et al., Methods Enzymol. 316:761-776, 2000 and Fritz J J et al., Methods Enzymol. 346:358-377, 2002. In vitro screening of the kinetic properties of hammerhead ribozymes is recognized to be a cost-efficient analytic step, enabling selection of ribozymes having optimal cleavage characteristics without the necessity of more expensive animal studies. Details of screening methods for determining efficacy of the ribozymes of the invention, including assays of activity and multiple turnover kinetic analysis using short RNA targets and full length targets, as well as assays of the ability of ribozymes expressed in stably transfected cells to reduce HSV yields in HSV-infected cells, are further described in the examples below.

Vectors

Although the ribozymes of the invention might be used in naked nucleic acid form, to increase stability and expression, the invention further provides vectors for expressing a ribozyme of the invention. Any vector compatible with a particular application of the invention might be used. For example, plasmid or virus-based vectors might be used. Examples of virus-based vectors include those based on lentiviruses, other retroviruses, adenovirus, adeno-associated virus, foamy viruses, and herpes viruses. See, e.g., Kay et al., Nature Medicine 7:33-40, 2001.

For specifically targeting cells permissive to HSV infection, the ribozymes of the invention are preferably included in an HSV expression vector (e.g, a non-replicating HSV-based vector). HSV vectors expressing the anti-HSV RNA ribozymes can, for example, be based on a prototype vector, 8117/43, a non-replicating recombinant of HSV-1 that lacks the essential immediate early gene (i.e., ICP4) and contains the E. coli LacZ gene driven by a hybrid promoter. The promoter can be a fusion between the HSV latency associated transcript (LAT) promoter and the Moloney Murine Leukemia Virus long terminal repeat. Although this virus cannot productively replicate outside of a helper cell line, it is able to establish a latent infection within the peripheral and central nervous system of mice, rats and rabbits. The hybrid promoter of this virus has been shown to be capable of expressing β-galactosidase for extended periods of time (Lokensgard J R et al., J Virol 68:7148-7158, 1994; Bloom D C et al., Gene Ther 1 Suppl 1:S36-S38, 1994).

To produce an HSV-based ribozyme-expressing vector, synthetic oligonucleotides encoding the ribozymes are cloned in a HSV recombination vector so as to place each ribozyme under the control of an HSV acute promoter. Any suitably constructed recombination plasmid can be utilized for this purpose, e.g., pDCB85 wherein the promoter-ribozyme cassette is flanked by the regions of the genome immediately upstream and downstream of the ICP4 promoter and coding region. These regions act as "recombination arms" that allow the promoter-ribozyme cassette to be inserted into the HSV-1 genome in place of ICP4 resulting in a replication-negative (i.e., ICP4⁻) HSV vector containing two copies of the promoter-ribozyme cassette, with one in each of the two short repeats. The recombination process is accomplished by co-transfecting virion DNA with the recombination plasmid into a helper cell line such as E5. Viral recombinants are subsequently identified, purified and characterized using known methods.

Ribozyme-Resistant Cell for Producing HSV-Vectored Ribozymes

The invention also provides a ribozyme-resistant cell for producing HSV-vectored ribozymes. In the case of a non-replicating HSV vector, e.g., one that is ICP4⁻, the vector can be propagated in a "helper" cell line (also known as a "complementing" or "packaging" cell line) that expresses the missing protein in trans. This can be achieved, e.g., using a cell line such as E5, which is based on Vero cells and expresses ICP4 (Shepard A A and DeLuca N A, J. Virol., 65:787-795, 1991). Nevertheless, those of skill in the art will recognize that any packaging cell line suitable for the purpose can be used.

The ribozyme-resistant packaging cell lines of the invention are designed to express a "hardened" version of the ribozyme target. Use of such cell lines is important because expression of an anti-HSV ribozyme in a packaging cell line would result in the production of ribozymes that inhibit viral replication and packaging. To avoid this, and thereby permit propagation of the ribozyme-expressing vectors, complementing cell lines can be constructed that produce their own "hardened" versions of the viral target mRNAs. Hardened versions of the targets are those that have been altered such that the ribozymes produced by the vector cannot cleave the targets (e.g., UL20, UL30, UL54 and ICP4) necessary for vector production within the packaging cell line.

Ribozyme-resistant cell lines can be made by introducing alterations into the coding sequences (e.g., silent mutations that change the nucleotide sequence but not the encoded amino acid sequence) of the target genes that make them resistant to the ribozymes using techniques such as site-directed mutagenesis. Complementing cell lines such as E5 cells (in the case of ICP4 targeting ribozymes) are then transfected with plasmids containing the mutagenized target genes. Those resulting cell lines exhibiting stable expression of the hardened targets are selected as packaging cell lines for producing vectors. Methods for producing mutagenized targets and their incorporation into cell lines are described in further detail in the examples below.

Stocks of ribozyme-expressing virus could also be prepared without the necessity of using a ribozyme-resistant packaging cell line constructed as described above, if, for example, a level of target mRNA production (e.g., resulting from the SV40 promoter in pZeoSV2) was achieved in the cell line sufficient to overcome cleavage by the ribozymes cloned into the non-replicating HSV vector.

Reducing HSV Replication in a Cell

The ribozymes of the invention can be used to prevent HSV replication in a cell as well as to prevent viral reactivation in latently infected cells by incorporating ribozymes directed against essential replicative genes of HSV into vectors capable of delivery of the ribozymes to the cell. The cell can be any cell type capable of infection by HSV, e.g. one actively or latently infected with the virus. Cell types particularly suitable for treatment with the ribozyme-targeting HSV vectors of the invention are cells of the nervous system, and affected tissues in contact with nerve endings (e.g., the cornea, conjunctiva, and mucosa) which are known to be susceptible to infection with HSV-1 or HSV-2.

EXAMPLES

Example 1

Hammerhead Ribozymes Targeting HSV mRNAs

1. Materials and Methods

Design of hammerhead ribozymes. Regions were selected in the target RNA containing NUX, where N represents any nucleotide, U represents uridine and X is any nucleotide except guanosine. Two stretches of antisense nucleotides that flank the conserved nucleotide sequence forming the catalytic domain between them were then designed, based on the target sequence surrounding the nucleotide X of the target. Nucleotide X was not base-paired with the ribozyme. The nucleotide sequences of each of the four HSV target genes (ICP4, UL20, UL30, UL54) were scanned for hammerhead cleavage sites (N-U-X) that were: 1) predicted to be in a single stranded region (not a base paired double stranded region) based on RNA folding programs (MFOLD 3.0) and 2) surrounded by flanking sequences that had a low G+C content. All ribozymes designed and tested employed a GUC target triplet, with the exception of human ICP4 Rz882, for which CUC was the target. To achieve highly active hammerhead ribozymes, helices I and III (which form the hammerhead portion of the ribozyme that is complementary to the target RNA sequence) were designed to contain no more than 12 base pairs.

Activity assays using short RNA targets. Ribozymes were synthesized and tested in vitro using end-labeled synthetic RNA oligonucleotides comprising the exact target sequence of the ribozyme. To ensure purity, both the RNA target and the ribozyme were gel purified prior to reaction, and the molar concentration of each was determined based on UV absorption. Denaturing gel electrophoresis was used to separate digestion products, and the extent of reaction was measured quantitatively using a Phosphorimager (Molecular Dynamics, Sunnyvale, Calif.).

Reaction time-course. Reaction time courses were evaluated under conditions consisting of 50-100 pmoles of target RNA in 10 mM $MgCl_2$, 40 mM Tris HCl, pH 7.5 (37° C.). After pre-incubation at 37° C., ribozyme was added at one tenth the concentration of substrate. Reaction aliquots were removed at intervals ranging from 1 minute to 2 hours for analysis of cleavage. Reactions were stopped by adding gel loading dye containing 95% formamide and 25 mM EDTA. Experimental conditions such as time of incubation, magnesium concentration, and ribozyme concentration were varied independently. Ribozymes requiring high magnesium concentrations or high ribozyme concentration for cleavage were eliminated from further consideration.

Multiple turnover kinetic analysis. Product release is frequently the rate-limiting step in ribozyme reactions. Therefore determining the activity of a particular ribozyme under substrate-excess (multiple turnover) conditions is often predictive of its utility in vivo. The appropriate interval for measuring reaction velocity was determined by a time-course experiment under multiple turnover conditions. Initial rates were measured when the amount of cleavage was linear with time, and when no more than 15% of substrate had been converted to product. Rates were measured at several intervals (e.g., 5, 10 and 20 min) to insure linearity. Samples were pre-incubated at 37° C. prior to initiation of cleavage, and contained 1-10 nM ribozyme and increasing concentrations of substrate RNA, while holding ribozyme concentration constant. Substrate concentrations greatly exceeded ribozyme concentration, this excess never being lower than 5-fold. Values for $V_{max}$ and $K_M$ were obtained by double reciprocal plots of velocity versus substrate concentration (Lineweaver-Burke plots) or by curve-fitting to the plot of [S] versus $V_0$. The turnover number $k_{cat}$ was determined by dividing $V_{max}$ by the ribozyme concentration.

Accessibility of the target site using full length targets. RNA assumes stable higher-order structures; accordingly, it must be determined that the target site for the ribozyme is accessible, e.g., that it is not internally base-paired within the mRNA. For this purpose, a secondary structure prediction (MFOLD) was first used, followed by experimental confirmation of accessibility.

For HSV-specific ribozymes, accessibility is tested by preparing clones of the desired cDNAs (e.g., ICP4, UL20, UL30 and UL54) in a T7 transcription vector (pT7/T3-19) using appropriate substrate DNA and primers. Run-off transcription is performed from each vector in the presence of $\alpha$-$^{32}$P-UTP, and the concentration of each RNA product is determined by its specific radioactivity. Equimolar ribozyme and full length target RNA are incubated for increasing intervals as described above for oligonucleotide targets. Products of the reaction are separated on 5% polyacrylamide gels containing 8M urea as denaturant, and dried gels are analyzed using a Phosphorimager. Preferred ribozymes are those that cleave their cognate target mRNAs in this assay with desirable kinetic properties, i.e., with high percentage of full length target cleaved (e.g., >85% cleaved) and high turnover number using oligonucleotide targets ($k_{cat}$ that is substantially >1 min$^{-1}$).

2. Results

Using the above-described criteria, a large number of synthetic ribozymes was designed to cleave mRNAs from HSV genes UL20, UL30, UL54 and ICP4. FIG. 1 shows the nucleotide sequences of several exemplary ribozymes fitting the criteria. These synthetic ribozymes were all of the 6-4-5 stem-loop-stem design. The cleavage sites of five of the six depicted HSV target mRNAs were G-U-C sequences, whereas a C-U-C sequence was present in the ICP4-882 ribozyme (ICP4 Rz882) targeting ICP4 mRNA. The hammerhead portions (helices I, III) of the synthetic ribozymes is complementary to the listed sequences, except for replacement of thymidine (T) with uridine (U). The exemplary ribozymes, having the 6-4-5 stem-loop-stem design shown in FIG. 1, had the following RNA sequences:

```
UL30 Rz933:  5' AAG GUC UGA UGA GCG CUU (SEQ ID NO:1)
                 CGG CGC GAA ACG AAC 3'

UL20 Rz135:  5' GAA CUC UGA UGA GCG CUU (SEQ ID NO:2)
                 CGG CGC GAA ACA AAA 3'

UL20Rz154:   5' CGG AAC UGA UGA GCG CUU (SEQ ID NO:3)
                 CGG CGC GAA ACG CGA 3'

UL54Rz233:   5' UUC UGC UGA UGA GCG CUU (SEQ ID NO:4)
                 CGG CGC GAA ACG AGA 3'

UL54Rz825:   5' UGC AUC UGA UGA GCG CUU (SEQ ID NO:5)
                 CGG CGC GAA ACC UGU 3'
```

```
                        -continued
ICP4Rz882:   5' ACG AAC UGA UGA GCG CUU (SEQ ID NO:6)
                 CGG CGC GAA AGG AUG 3'
```

Figure 2:
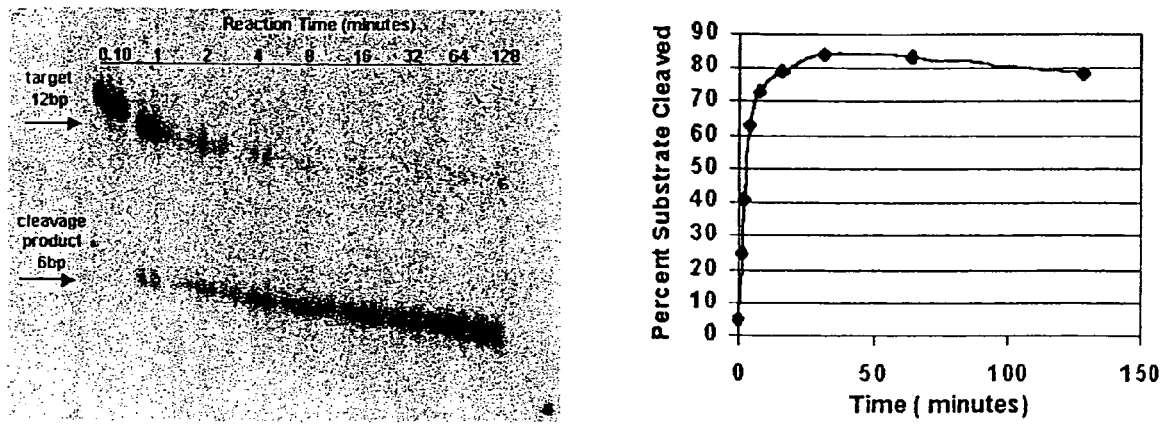
FIG. 2 is an autoradiogram (A) and a graph (B) showing a time course of RNA target cleavage, and percentage of target cleaved, respectively, by ribozyme UL20-154.

Activity assays and reaction time-course. RNA targets and ribozymes were chemically synthesized with perfectly complementary sequences, and the substrate targets were end-labeled with $^{32}$P-ATP. The test to assay activity was a time course to determine the rate at which the ribozymes cleaved the target and the percentage of target that was finally cut. FIG. 2A is an autoradiogram from a study of ribozyme UL20-154, showing the gradual disappearance of the target band (i.e., the 12 bp target) and concomitant appearance of increasing amounts of the resultant 6 bp cleavage product. Next, the percentage of substrate that was cut as a function of time was determined for a cleavage reaction with the same ribozyme, i.e., UL20-154. The results, shown in FIG. 2B, demonstrated high efficiency of this ribozyme, which cleaved more than 70% of the target within several minutes, and about 85% of the target within approximately 35 minutes.

TABLE 1

Kinetics of Hammerhead Ribozymes With Synthetic HSV RNA

| HSV Target Gene | $Mg^{+2}$ mM | $k_{cat}$ (min$^{-1}$) | $K_m$ (uM) | $k_{cat}/K_m$ (uM$^{-1}$ min$^{-1}$) |
|---|---|---|---|---|
| ICP4-581 | 20 | 15.9 | 52.8 | 0.301 |
| UL20-135 | 20 | 0.1 | 5.6 | 0.014 |
| UL20-154 | 5 | 27.8 | 1.8 | 15.886 |
| UL30-933 | 20 | 12.8 | 4.7 | 2.723 |
| UL54-825 | 5 | 51.3 | 4.4 | 11.659 |

Figure 3:
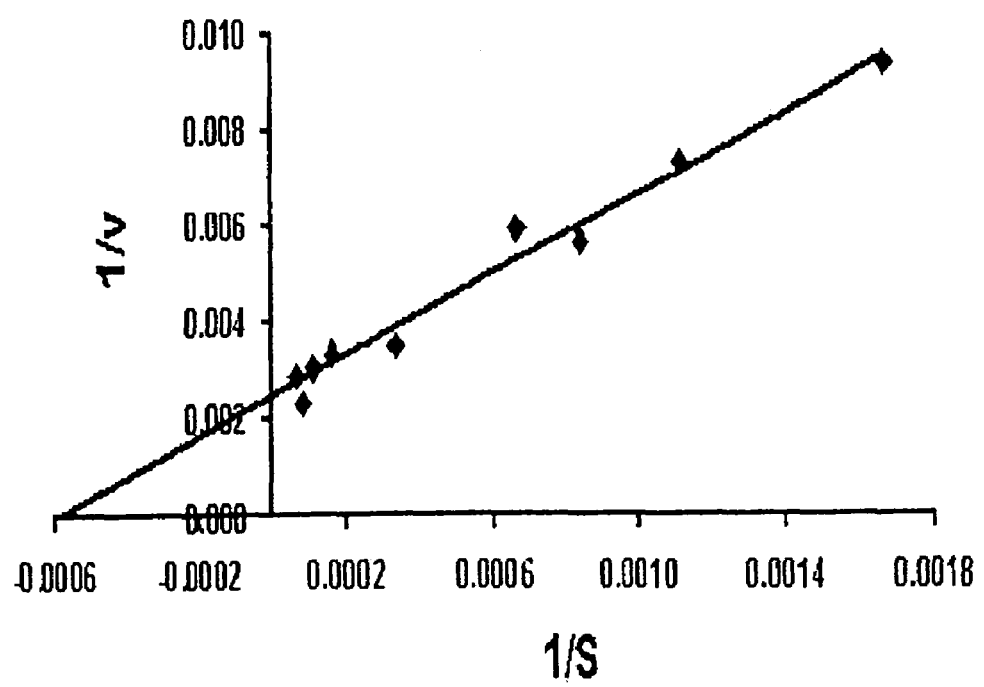
FIG. 3 is a graph showing a Lineweaver-Burke plot of ribozyme cleavage of a synthetic HSV RNA target. Least squares regression analysis generated a best fit line y=4.213+0.0024 with a correlation coefficient of $R^2$=0.978.

Ribozyme activity under substrate-excess conditions. Activity of ribozymes was tested under substrate-excess conditions as described. The turnover number $k_{cat}$ was determined by dividing $V_{max}$ by the ribozyme concentration. FIG. 3 shows a typical Lineweaver-Burke plot for the UL20-154 ribozyme in 5 mM $Mg^{+2}$. Table 1 shows results of kinetic assays of five tested ribozymes (i.e., ICP4-581, UL20-154, UL30-933, UL54-825). Four of these demonstrated a $k_{cat}$ of substantially >1 min$^{-1}$, indicating very efficient cutting of their respective synthetic substrate RNAs. By contrast, an observed $k_{cat}$ value for the UL20-135 ribozyme of substantially <1 min$^{-1}$ indicated that this ribozyme was much less effective.

Example 2

Ribozyme-Mediated Inhibition of HSV Replication in Cultured Cells

Construction of stably transfected cell lines expressing the anti-HSV-1 ribozymes. Plasmids containing synthesized DNA templates encoding the ribozymes of the invention are constructed using the parent plasmid pTRUF21. This plasmid contains the ribozyme-coding sequence under the control of the CMV IE enhancer/chicken β-globin hybrid promoter, and also contains the neomycin resistance gene in order to allow for selection of stable cell lines. Stably transfected Vero cells are constructed by transfecting semi-confluent monolayers in 60 mm dishes with the plasmids containing the ribozyme expression cassettes. The transfections are performed using Lipofectamine 2000 (InVitrogen, Carlsbad, Calif.) according to the manufacturer's recommendations. Following transfection, the cells are cultured in media containing 500 μg/ml G418 (Geneticin, InVitrogen), and several clonal lines of neomycin-resistant cells are isolated for each ribozyme construct, either by use of cloning cylinders or by limiting dilution. Following several passes of the lines, relative levels of ribozyme expression are assessed by QT-PCR. In addition to the cell lines expressing the ribozymes, a control cell line is used. The control cell line is constructed to contain the parent pTRUF21 plasmid with the CMV/chicken β-actin promoter expressing green fluorescent protein (GFP).

Assay of the ability of the ribozymes to reduce HSV yields in infected cells. The ability of the ribozymes expressed by the stably transfected cell lines is assessed by performing single and multi-step viral replication assays on at least two separate cell lines for each ribozyme. All replication assays are performed in triplicate in 35 mm dishes containing just-confluent monolayers of each cell line. Assays include as controls the GFP-expressing cell line (and the parent Vero cell line). Infections are performed by removing media from the dishes and replacing with 0.3 ml of complete medium (Minimal Essential Medium, Gibco Life Technologies, Gaithersburg, Md., with 10% fetal bovine serum and antibiotics) containing wild-type HSV-1 strain 17syn+. This inoculum is allowed to adsorb onto the cells for 1 hour (at 37° C., 5% $CO_2$ with humidity), at which point it is removed and replaced with 2.5 ml complete medium. The dishes are then incubated (at 37° C., 5% $CO_2$ with humidity) for the appropriate time intervals, and harvested.

For single-step growth curve analysis, the cells are infected at a mulitiplicity of infection (m.o.i.) of 3, and dishes are harvested at 0, 4, 8, 12 and 18 hours post-infection. For multi-step growth analysis, the cells are infected at a m.o.i of 0.001, and dishes are harvested at 0, 4, 12, 24, 48, 72 and 96 hours post-infection. The method of harvesting can vary slightly, depending on the assay to be performed (described below).

Example 3

Ribozyme-Resistant Packaging Cell Line

Construction of packaging cell lines expressing "hardened" ribozyme targets. The ribozymes of the invention can be delivered to cells in an HSV vector. For example, the ribozymes can be delivered in a non-replicating HSV vector that contains a deletion in the ICP4 gene (Burton E A et al., Curr Opin Biotechnol 2002, 13:424-428). This vector can be propagated in the helper cell line E5. The E5 cell line is based on Vero cells, and has been engineered to contain the ICP4 gene stably integrated into its genome. To circumvent the problem of the HSV-targeting ribozyme cleaving the viral RNA needed for HSV vector propagation, a ribozyme-resistant E5 cell line is constructed that is capable of resisting the destructive effect of the ribozymes of the invention. To achieve this, E5 cells are transfected with plasmids containing the mutagenized target genes, following site-directed mutagenesis procedures described below. Stable cell lines demonstrating expression of the hardened target mRNAs are then selected for use as packaging cell lines.

Site-directed mutagenesis. Individual genes targeted by the ribozymes are cloned by PCR in plasmid pCR2.1 (Invitrogen, Carlsbad, Calif.) using HSV DNA as template, or by restriction-enzyme digestion and cloning directly into the pZeoSV2 expression plasmid. To produce "hardened" RNA targets, i.e., RNA target sequences not cleavable by the ribozymes, two or three nucleotide changes are made in each gene that remove the ribozyme target site, yet preserve the coding information, as shown by the examples in Table 2. Nucleotide substitutions are introduced using a site-directed mutagenesis kit from Stratagene, which permits the co-conversion of several linked nucleotides. In the case of UL30, mutagenesis is performed on a SnaB1-Nhe1 restriction fragment of 778 nt, which is then recloned in the 3.7 kb reading frame. These sites are unique and flank the 5' region of the gene, in which several potential cleavage sites have been identified.

TABLE 2

Nucleotide Sequence of Wild-Type and "Hardened" RNA Targets for Ribozymes

| HSV mRNA | Wild-type target | "Hardened"* target |
|---|---|---|
| ICP4 (position 882) | CAUCCUCUUCGU (SEQ ID NO:7) | CUUCAUCCUCGU (SEQ ID NO:78) |
| UL20 (position 135) | UUUUGUCAGUUC (SEQ ID NO:9) | UUUCGUGAGCUC (SEQ ID NO:10) |
| UL20 (position 154) | UCGCGUCUUCCG (SEQ ID NO:11) | UCACGCCUCCCG (SEQ ID NO:12) |
| UL30 (position 933) | GUUCGUCACCUU (SEQ ID NO:13) | AUUCGUGACAUU (SEQ ID NO:14) |
| UL54 (position 233) | UCUCGUCCAGAA (SEQ ID NO:15) | UCCCGCCCCGAA (SEQ ID NO:16) |
| UL54 (position 825) | ACAGGUCAUGCA (SEQ ID NO:17) | ACAAGUGAUGCA (SEQ ID NO:18) |

Example 4

HSV-Vectored Ribozymes

Construction of non-replicating HSV vectors. Non-replicating HSV vectors expressing the anti-HSV RNA ribozymes are constructed according to the strategy shown schematically in FIG. 4. The prototype of these vectors, 8117/43, is a non-replicating recombinant of HSV-1 that lacks the essential immediate early gene (ICP4) and contains the *E. coli* LacZ gene downstream of a hybrid promoter that is a fusion between the HSV LAT promoter and the Moloney Murine Leukemia Virus LTR. This vector has been shown to be capable of establishing a latent infection within the peripheral and central nervous systems of mice, rats and rabbits. Its hybrid promoter is capable of expressing β-galactosidase for extended periods of time (Lokensgard J R et al., J Virol 68:7148-7158, 1994; Bloom D C et al., Gene Ther 1 Suppl 1:S36-S38, 1994.)

To construct the ribozyme-expressing vectors, synthetic oligonucleotides encoding the ribozymes are cloned into the HSV recombination vector pDB85, so as to place each ribozyme under the control of an HSV acute promoter (FIG. 4). In plasmid pDB85, the promoter-ribozyme cassette is flanked by the region of the genome immediately upstream and downstream of the ICP4 promoter and coding region, and the cassette is inserted into the HSV-1 genome in place of ICP4. This results in an ICP4(−) HSV vector containing two copies of the promoter-ribozyme cassette (one in each of the two short repeats). The recombination process is accomplished by co-transfecting virion DNA with the recombination plasmid into the E5 helper cell line by calcium-phosphate precipitation. Viral recombinants are subsequently identified, purified and characterized as described (Bloom D C, in Methods in Molecular Biology, Herpes Simplex Protocols, Brown S and MacLean A, eds., Humana Press, 1998).

Growth, purification, and titration of the HSV recombinants for inoculation. The recombinant (ICP4−) HSV vectors are propagated on the appropriate "hardened" helper cell lines, prepared as described above. The HSV virions produced by the cell lines are purified from cellular debris by centrifugation through a gradient of, e.g., 5-15% Ficoll 4000 in PBS. This purification step is important because without it, cytopathology of producer cells can be seen when the non-replicating HSV mutants are used to infect cells in culture at high multiplicities of infection (m.o.i. >1). This result is thought to be largely due to the carry-over of cellular debris and viral peptides toxic to the cells at high concentration. Purification of the HSV vectors in the disclosed manner eliminates cytopathology at m.o.i. of less than 5. The viral band collected from the gradient is pelleted through PBS by ultracentrifugation, and the resulting pellet is resuspended in Modified Eagle's Medium (MEM) supplemented with 10% Fetal Bovine Serum (FBS), aliquoted and maintained at −80° C. An aliquot of each stock is titrated by standard techniques on E5 cells to determine the number of infectious particles present.

Example 5

Reduction of HSV-1 Replication by HSV-Vectored Ribozymes In Vitro

Following construction, characterization, and purification, HSV-ribozyme-expressing vectors can be analyzed for their ability to interfere with wild type (wt) HSV infection in vitro. In a typical assay, cultured epithelial cells of the skin are infected with the ribozyme-containing HSV vectors, and used to test the ability of these vectors to prevent or reduce viral replication following infection of the cells with wt HSV-1. Single-step and multi-step viral replication assays are performed essentially as described above, except that the non-replicating vectors are added to the cells at selected times in relation to the time of addition of the HSV-1, i.e., either prior to HSV infection, (e.g., 12 hours before), at the time of infection (co-infection with vector and HSV-1), or post-HSV-1 infection (e.g., 4 hours after). Performance of the replication assays in this manner allows assessment of both the capability of the vector-expressed ribozymes to interfere with HSV-1 infection and of the optimal time frame for action by the ribozymes.

Example 6

Reduction of HSV-1 Replication by HSV-Vectored Ribozymes In Vivo

This example describes an assay for testing the ability of HSV-vectored ribozymes of the invention to reduce the production of HSV-1 in a rabbit model of corneal infection (viral keratitis) caused by latent HSV infection in the trigeminal nerve. A latent infection of trigeminal nerves in rabbits can be established using established procedures (Shimomura Y et al., Invest Ophthalmol Vis Sci 26:121-125, 1985). For example, the corneas of rabbits anesthetized by an intramuscular injection of ketamine and xylazine are scratched in a cross hatch pattern with a needle, then treated with a 25 μl inoculum containing $2\times10^5$ PFU of the 17 syn+ strain of HSV-1. This procedure results in clinical evidence of corneal inflammation and viral shedding in the tear film within 3-5 days in 100% of the animals. Viral shedding is confirmed by swabbing the conjunctiva with Dacron swabs which are swirled in medium, followed by determination of the viral number by PFU titration with rabbit epidermal cells. Observations including gradual resolution of the viral keratitis over the next 5 to 7 days, inability to detect viral particles in the tear film, and clearing of the cornea are indicative of latency of the virus in the trigeminal ganglion.

Latent HSV infection is reactivated experimentally in these animals by epinephrine iontophoresis. Briefly, rabbits are anesthetized with ketamine and xylazine. A 10 mm diameter Delrin eye cup with an 8 mm diameter internal well with a platinum electrode is placed on the cornea and the cathode electrode is attached to a shaved area of the rabbit's ear. The well is filled with a 0.01% epinephrine solution, and a direct current (0.8 mAmps, 7 Volts) is applied for 8 minutes. Within three days, clinical symptoms of HSV keratitis and viral shedding occur in approximately 80% of the eyes.

Following reactivation, the level of HSV shedding in the tears is measured using placing Schirmer strips (Allergan, Houston, Tex.) in the inferior cul-de-sac (Robert P Y et al., J Med Virol 66:506-511, 2002). Strips are applied to the lower formix and left long enough to wet the strips to 25 mm. The tear-soaked strips are cut into 5 mm pieces and immersed in a phosphate buffered saline solution. Lacrimal fluid residues are removed by heating in a microwave oven for 1 minute and incubating at room temperature for 2 hours. DNA is then extracted by matrix affinity chromatography using a QuiAmp blood kit (Qiagen, Courtaboeuf, France). PCR amplification of the extracted DNA is performed using quantitative TaqMan PCR as described above.

Transduction of rabbit corneal and trigeminal cells with herpes-vectored ribozymes. Corneas of latently infected rabbits are injected intrastromally with 100 μl of saline containing the herpes-vectored ribozyme. Optimal numbers of infectious herpes vector particles for injection are expected to be in the range of $10^4$ to $10^6$ infectious vector particles, as determined using a reporter vector in varying concentrations. Injection is achieved, e.g., using a 30# hypodermic needle visualized under an operating microscope. Alternative methods of the vector infection include iontophoresis of the vector, collagen shield soaked in vector following scarification, and use of a suction trephine.

To test the ability of the herpes-vectored ribozymes to decrease or prevent the reactivation of HSV-1, rabbits are infected with the 17 syn+ strain of the virus on day 0. In this method, a large number of viral particles is generally shed in the tear film within 3-5 days following the infection, with viral shedding returning to baseline by 30 days post infection. On day 30, intrastromal injections of the herpes-vectored active ribozyme and two controls consisting of herpes-vectored inactive ribozyme and saline are performed. Seven days following the injection, when viral presence in the tears is minimal, epinephrine iontophoresis is used to reactivate the latent HSV-1 virus in the trigeminal ganglia, leading to viral shedding. The level of viral shedding in the tear film is measured starting 72 hours following the iontophoresis using PCR on Schirmer strips as described earlier, and results are analyzed comparing viral shedding observed in animals injected with control and herpes-vectored active ribozymes.

Example 7

Ribozyme-Mediated Reduction in Plaque Formation

Four cloned cell lines containing the ICP4-588 ribozyme, three cloned cell lines stably expressing the UL20-154 ribozyme, and two clones expressing the UL54-825 ribozyme were made. The ability of the ribozymes to reduce plaque formation was investigated. Briefly, immortalized rabbit epidermal skin cells (RS) that were stably transfected with the pTR-ICP4-588 ribozyme or non-transfected cells were cultured in 6 well plates to confluency then infected with HSV 17 syn+ virus at a MOI of 3:1. After 24 hours the plates were washed, fixed and stained to reveal plaques. Plaque formation in cultures of cells expressing the ribozymes was dramatically reduced compared to non-transfected cells as indicated by the nearly confluent lawn of blue staining cells. Furthermore, the number of plaque forming units (pfu) per culture was reduced approximately 90% as determined by titration of infectious virus extracted from the cell cultures 24 hours after infection. These results in stably transfected cells were supported by other results in E5 cells that were transiently transfected with a plasmid expressing the ICP4-581 ribozyme. An ethidium bromide-stained agar gel of RT-PCR reaction products showed an approximately 80% reduction in the level of ICP4 mRNA by the ribozyme compared to E5 cells that were transfected with the packaging vector without the ribozyme. In summary, these data show that the stable expression of the ICP4-588 ribozyme in RS cells results in an 8-fold reduction in infectious yield 24 hours after infection.

Example 8

Establishment of Latent HSV Infection and Reactivation in Rabbits

A latent infection in the trigeminal ganglion of rabbits was established by inoculating rabbit corneas with 25 µl of 2×10$^5$ pfu of the 17 syn+ strain of HSV 1. All 10 eyes of the five rabbits that were inoculated showed evidence of active epithelial and stromal infection within 4 days. This was confirmed by the presence of HSV DNA in conjunctival swabs. On resolution of the primary infection, the trigeminal ganglia of the rabbits was harvested and showed the presence of HSV DNA by PCR indicating the establishment of latent infection. Previous experiments by others using epinephrine iontophoresis on rabbits latently infected with the 17syn+ strain of HSV-1 showed a reactivation rate of almost 90%. In contrast, only 10% of the rabbits latently infected with the 17ΔPst strain of HSV shed virus in their conjunctival sacs which is consistent with the known inefficient reactivation of this strain of HSV.

Example 9

Infection of Trigeminal Nerves in Rabbits by the HSV-LacZ Vector

Trigeminal neurons were infected with a Herpes vector by ocular instillation. β-galactosidase activity, which is detected as blue reaction product, was present in numerous trigeminal neuron cell bodies and axons 72 hours following corneal intrastromal injection of the Herpes vector expressing LacZ reporter gene. This was confirmed in formalin-fixed, paraffin sections of the trigeminal nerve as seen in a Nomarski interference contrast photomicrograph. Numerous axons/dendrites which appeared as long streaks of blue stained segments were present, together with the large sensory neuron bodies. In addition, β-galactosidase activity was present in the corneal limbal area. On histological examination, the β-galactosidase activity was seen predominantly in the subepithelial stromal tissue in keratocytes. There was also some discrete punctate staining in some epithelial cells. Similar staining patterns were seen in rabbits infected by placing the tagged Herpes vector in a suction ring placed on the cornea for 10 minutes.

Other Embodiments

While the above specification contains many specifics, these should not be construed as limitations on the scope of the invention, but rather as examples of preferred embodiments thereof. Many other variations are possible.

---

What is claimed is:

1. A ribozyme that specifically cleaves a target RNA sequence encoded by a HSV gene UL20, having the nucleotide sequence set forth in SEQ ID NO: 3.

2. The ribozyme of claim 1, wherein the ribozyme is present in a hammerhead configuration.

3. The ribozyme of claim 1, wherein the ribozyme is comprised within a plasmid or viral vector.

4. The ribozyme of claim 1, wherein the ribozyme is comprised within a cell.

5. A ribozyme having a nucleotide sequence that specifically cleaves a target RNA sequence encoded by a HSV gene UL20, wherein the nucleotide sequence is SEQ ID NO: 3.

6. The ribozyme of claim 5, wherein the ribozyme is comprised within a plasmid or viral vector.

7. The ribozyme of claim 5, wherein the ribozyme is comprised within a cell.

8. A ribozyme-resistant cell for producing a HSV expression vector encoding an anti-HSV ribozyme, the cell comprising at least one nucleotide sequence encoding a portion of an HSV gene, the nucleotide sequence having been modified to not be cleavable byte ribozyme, the ribozyme having the nucleotide sequence set forth in SEQ ID NO: 3.

* * * * *